United States Patent
Baker et al.

[11] Patent Number: 6,071,271
[45] Date of Patent: *Jun. 6, 2000

[54] CARDIOPULMONARY CATHETER SYSTEM

[75] Inventors: Clyde Baker, South Jordan; Gary L. Crocker, Salt Lake City, both of Utah; Carl A. Swindle, Dana Point, Calif.

[73] Assignee: Baxter Research Medical, Inc., Midvale, Utah

[*] Notice: This patent issued on a continued prosecution application filed under 37 CFR 1.53(d), and is subject to the twenty year patent term provisions of 35 U.S.C. 154(a)(2).

[21] Appl. No.: 08/924,383

[22] Filed: Sep. 5, 1997

Related U.S. Application Data

[60] Provisional application No. 60/025,503, Sep. 5, 1996.

[51] Int. Cl.⁷ .................................................. A61M 25/00
[52] U.S. Cl. ............................ 604/500; 604/96; 604/523; 604/532
[58] Field of Search ..................................... 604/500, 506, 604/507, 508, 96, 523, 532, 536

[56] References Cited

U.S. PATENT DOCUMENTS

| | | | |
|---|---|---|---|
| 5,423,745 | 6/1995 | Todd et al. | 604/53 |
| 5,433,700 | 7/1995 | Peters | 604/4 |
| 5,478,309 | 12/1995 | Sweezer et al. | 604/4 |
| 5,558,644 | 9/1996 | Boyd et al. | 604/96 |
| 5,613,937 | 3/1997 | Garrison et al. | 600/201 |
| 5,616,137 | 4/1997 | Lindsay | 604/264 |
| 5,618,306 | 4/1997 | Roth et al. | 606/205 |
| 5,618,307 | 4/1997 | Donlon et al. | 606/205 |
| 5,620,418 | 4/1997 | O'Neill et al. | 604/96 |
| 5,772,642 | 6/1998 | Ciamacco, Jr. et al. | 604/500 |
| 5,810,757 | 9/1998 | Sweezer, Jr. et al. | 604/523 X |
| 5,817,071 | 10/1998 | Dewindt et al. | 604/523 X |

FOREIGN PATENT DOCUMENTS

| | | |
|---|---|---|
| WO 96/21489 | 7/1986 | WIPO . |
| WO 96/32882 | 10/1996 | WIPO . |

*Primary Examiner*—John D. Yasko
*Attorney, Agent, or Firm*—Workman, Nydegger & Seeley

[57] ABSTRACT

A catheter system for use in minimally invasive cardiac surgical procedures. The catheter system diminishes certain trauma generally associated with invasive cardiac procedures while providing aortic occlusion, extracorporeal circulation, cardiac arrest, and cardiac venting. The catheter system provides a minimally invasive and simplified system that performs total cardiopulmonary bypass with ease of insertion, improved whole body profusion, and shortened recovery periods. The catheters are refined, with reduced diameters and specialized functions for maximum control of each aspect of cardiopulmonary bypass.

40 Claims, 3 Drawing Sheets

CARDIOPULMONARY CATHETER SYSTEM

This application claims the benefit of provisional application No. 60/025,503 filed Sep. 5, 1996.

BACKGROUND OF THE INVENTION

1. The Field of the Invention

The present invention is directed generally to methods and apparatus for employing blood management during surgical procedures. More specifically, the present invention is directed to methods and apparatus for employing blood management during cardiac surgical procedures wherein cardiac arrest is induced and extracorporeal circulation and venting of the heart are provided.

2. Related Application

Benefit of the earlier filing date of Provisional Patent Application Ser. No. 60/025,503, filed Sep. 5, 1996, is claimed for this application under Section 119(e) of Title 35 of the United States Code.

3. The Relevant Technology

During surgical procedures involving the heart, it is often beneficial or necessary to provide life support, a bloodless surgical field, and a flaccid heart. Generally speaking, the procedure by which these are accomplished is known as cardiopulmonary bypass. Conventionally, in order to access the heart to initiate cardiopulmonary bypass, a surgeon first exposed the thoracic cavity via a central incision down the breastbone in a procedure known as a "median sternotomy," and dissected away tissue overlying the heart. A significant interest has developed in decreasing the extent of invasiveness necessary to perform cardiopulmonary bypass, with the intent to increase the effectiveness and success of the procedure.

For example, U.S. Pat. No. 5,478,309 by Sweezer et al., (hereinafter Sweezer et al.), discloses an approach for achieving total cardiopulmonary bypass during heart surgery utilizing a two catheter system without the need for a median sternotomy. A venous perfusion catheter is inserted peripherally into the atrial-caval junction, with two balloons blocking the flow of blood into the right atrium. This catheter provides the venous return to the cardiopulmonary bypass machine. An arterial perfusion catheter is inserted peripherally into the ascending aorta just above the coronary artery junction and provides aortic occlusion, aortic root venting, left ventricular decompression, aortic root cardioplegia delivery, and delivery of oxygenized arterial blood. However, in order to accommodate its multiplicity of functions, the arterial perfusion catheter must be substantially enlarged.

Similarly, U.S. Pat. No. 5,433,700 by Peters, (hereinafter Peters), discloses a process for inducing cardioplegic arrest and maintaining peripheral cardiopulmonary bypass utilizing only two catheters. This process positions a catheter into the right atrium via insertion through a femoral vein. This catheter employs two inflatable cuffs to allow isolation of the right atrium, and provides venous return to the cardiopulmonary bypass machine. The process additionally positions a catheter in the ascending aorta via insertion through a femoral artery. The arterial catheter occludes the ascending aorta, introduces cardioplegia, vents the left heart, and delivers oxygenated blood into arterial circulation. Yet, as in Sweezer et al., the Peters approach requires a significantly enlarged arterial catheter for performing a multiplicity of functions.

Still another approach is disclosed in U.S. Pat. No. 5,558,644 by Boyd et al., (hereinafter Boyd et al.). Specifically, Boyd et al. discloses a system for inducing cardioplegic arrest and sustaining cardiopulmonary bypass comprising a retrograde delivery catheter for occluding the coronary sinus, a venous cannula for withdrawing blood from a peripheral vein, an elongated arterial catheter inserted through the femoral or brachial artery for occluding the ascending aorta, an arterial return cannula for whole body perfusion, and a catheter placed in the pulmonary artery for venting the left atrium. Essentially, Boyd et al. attempts to minimize invasiveness by using at least five separate catheters.

Although substantial effort has been expended in designing various systems that look promising for decreasing the extent of invasiveness necessary to perform cardiopulmonary bypass, none has proven effectively workable in practical application. Consequently, the desired improvements in the effectiveness and success of the procedures requiring cardiopulmonary bypass have not followed.

SUMMARY AND OBJECTS OF THE INVENTION

It is therefore a primary object of the present invention to provide improved methods and apparatus for a catheter system for use in cardiac surgical procedures.

It is another object of the present invention to provide methods and apparatus for providing extracorporeal circulation, cardiac arrest, and cardiac venting during cardiac surgical procedures.

Still another object of the present invention is to provide methods and apparatus for decreasing the extent of pain and time of post-operative recovery involved with cardiac surgical procedures.

Another object of the present invention is to provide methods and apparatus for diminishing certain trauma generally associated with invasive cardiac surgical procedures.

A further object of the present invention is to provide methods and apparatus for improved functionality of the catheter system.

It is still another object of the present invention to provide methods and apparatus for improved aortic occlusion.

Another object of the present invention is to provide methods and apparatus for improved whole body perfusion.

Yet another object of the present invention is to provide methods and apparatus for ease of insertion and positioning of the catheter system.

Another object of the invention is to provide methods and apparatus for lessening the risk of dislodgement of material from the inner surface of the aorta upon insertion of an arterial return catheter.

To achieve the foregoing objects, and in accordance with the invention as embodied and broadly described herein, the present invention is directed to new and useful methods and apparatus for a catheter system for use in cardiac surgical procedures. This invention diminishes certain trauma generally associated with invasive cardiac procedures while providing aortic occlusion, extracorporeal circulation, cardiac arrest, and cardiac venting.

One presently preferred embodiment of the present invention includes three separate catheters providing a simplified system with ease of insertion that performs total cardiopulmonary bypass with improved whole body perfusion. These catheters are refined, with reduced diameters and specialized functions for maximum control of each aspect of cardiopulmonary bypass. The three catheter system of the present invention preferably includes an aortic occlusion catheter, a femoral access venous return catheter, and a femoral access arterial return catheter.

Another embodiment of the present invention includes four separate catheters providing a simplified system with ease of insertion that performs total cardiopulmonary bypass with improved whole body perfusion. The four catheter system of the present invention preferably adds a jugular access catheter to the three catheter system described above.

To use the four catheter system of the present invention, the first step preferably includes insertion and proper placement of each catheter. Preferably, the extracorporeal circulation is commenced just prior to or concurrently with cardiac arrest. An inflatable balloon on the aortic occlusion catheter is inflated to occlude the ascending aorta. The heart is stopped, preferably by perfusing the heart with potassium solution or cardioplegia through the aortic occlusion catheter. After the heart has been stopped, the aortic occlusion catheter is utilized to vent the left ventricle and the jugular access perfusion catheter perfuses cardioplegia solution into the coronary sinus. Venous blood is withdrawn from the patient's circulation through the venous return catheter inserted through a femoral vein. Arterial blood is returned to the patient through the arterial return catheter inserted into a femoral artery.

These and other objects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention will be rendered by reference to specific embodiments thereof which are illustrated in the appended drawings. Understanding that these drawings depict only typical embodiments of the invention and are not therefore to be considered to be limiting of its scope, the invention in its presently understood best mode for making and using the same will be described and explained with additional specificity and detail through the use of the accompanying drawings in which.

DETAILED DESCRIPTION OF THE PREFERRED EMBODIMENTS

Figure 1:
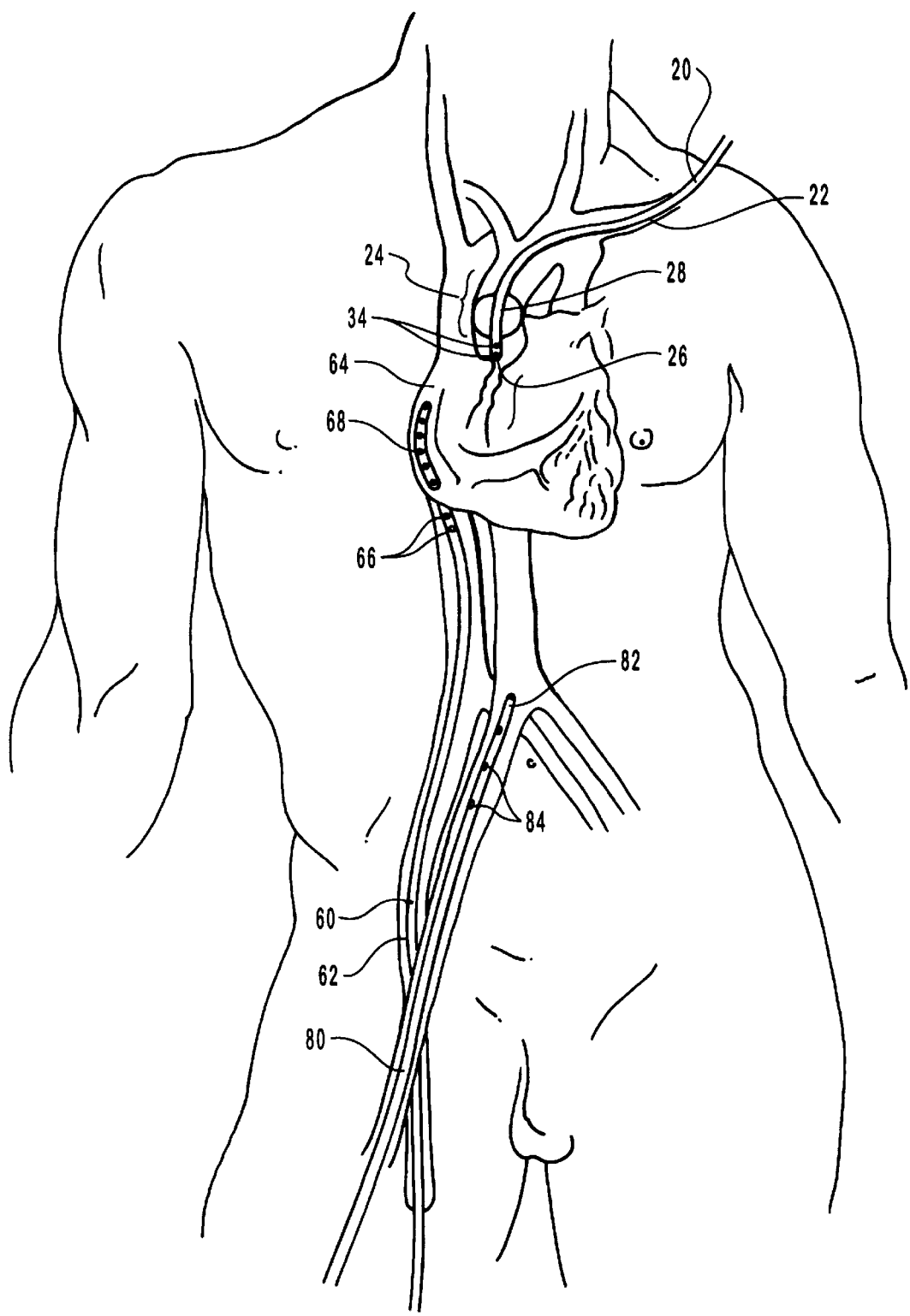
FIG. 1 is an illustration of a three-catheter system in accordance with the present invention in situ.

The present invention relates to methods and apparatus for a catheter system for use in cardiac surgical procedures. This invention diminishes certain trauma generally associated with invasive cardiac procedures while providing aortic occlusion, extracorporeal circulation, cardiac arrest, and cardiac venting.

The conventional approach in many cardiac surgical procedures required an open and exposed thoracic cavity. Less invasive approaches ultimately developed, but many of these have not proved to be useful in practice. For example, certain approaches combined too many functions into each catheter making insertion of the catheters difficult at best. These bulky, multi-function catheters offered limited variability for less than optimum systems. Alternative approaches failed to result in acceptable levels of perfusion of the greater vessels.

It has been appreciated in connection with the present invention that the Sweezer et al. approach, by confining total cardiopulmonary bypass including cardioplegia and venting, into two catheters, requires a substantially enlarged arterial catheter which limits the effectiveness of the system. In particular, it is the lumen utilized for whole body perfusion which accounts for and demands a significant portion of the internal space of the catheter. However, this high demand on the available internal space of the catheter, in concert with the demands from the other lumens necessary for venting, aortic root occlusion, and cardioplegia delivery, produces a catheter which is prohibitively enlarged; insertion may be difficult or even impossible in certain patients. Yet, reduction in the size of the catheter by decreasing the space apportioned for whole body perfusion results in inadequate perfusion.

Poiseuille's Law further illustrates the point. The volume flow rate Q of a viscous fluid like blood is influenced by the pressure, radius, and length of a particular tube, and the viscosity of the fluid. For example, Q is inversely proportional to the length of the tube; the longer the tube, the greater resistance to the rate of flow. In addition, Q is proportional to the radius $R^4$. A reduction in the radius of a tube by one-half reduces the volume flow rate to one-sixteenth of its original value. J. Cutnell and K. Johnson, *Physics*, Wiley, (1989). Thus, the arterial catheter in Sweezer et al. must overcome the inherent decrease in flow rate associated with the length of the catheter. It should be appreciated that if the diameter of the catheter is also reduced to facilitate insertion, the flow rate is substantially diminished.

Furthermore, even if the initial insertion were not an obstacle, the enlarged arterial catheter may damage the internal surface of the aorta and dislodge material from the vessel wall upon maneuvering the catheter through the femoral artery and up into the ascending aorta. Perfusion solely through the femoral artery directs such dislodged material into the greater vessels (innominate, left subclavian, and left common carotid) which provide oxygenated blood to the brain and upper body. The dislodged material may become trapped in the smaller arteries feeding the brain resulting in an embolism or stroke.

Similarly, the Peters process requires insertion of a substantially enlarged arterial catheter. In addition to the deficiencies detailed above with respect to Sweezer et al., the multiplicity of functions performed by the arterial catheter adds extreme bulk and complexity to the process. Furthermore, troubleshooting is hampered by uncertainty as to where problems reside; any error or malfunction in any part of the arterial catheter likely entails removal of the whole device.

It has also been appreciated in connection with the present invention that the aortic catheter in Boyd et al., by blocking and limiting the area in the descending aorta and aortic arch available for upper body perfusion, may severely limit arterial blood flow through the greater vessels and into the brain. It was demonstrated herein above that a decrease in the area available for blood flow by one-half decreases the flow rate to one-sixteenth. Thus, the area blocked by the aortic catheter in Boyd et al. will necessarily decrease the flow rate of oxygenated blood to the head and upper body. Any attempt to increase the flow rate by increasing the velocity of the fluid exiting the catheter may actually dislodge and direct plaques and other debris into the head and neck.

Realizing that there is a constant tension between providing a catheter small enough to offer ease of insertion into and removal from a vessel, but also large enough to provide appropriate perfusion levels at acceptable velocities, the present invention departs from the conventional minimally invasive catheter systems. The terms proximal and distal are utilized herein to facilitate the description of the elements of the present invention. Proximal as utilized herein refers to a direction or location which is closer to the heart than another element, while distal refers to a direction or location which is further from the heart than another element.

One preferred system in accordance with the present invention comprises three specialized catheters. As illustrated in FIG. 1, this three-catheter system includes an aortic occlusion catheter 20, a femoral access venous return catheter 60, and a femoral access arterial return catheter 80, for a system providing aortic occlusion, extracorporeal circulation, cardiac arrest and cardiac venting.

The aortic occlusion catheter 20 of the present invention is specifically designed for insertion into a peripheral vessel. The aortic occlusion catheter 20 terminates in a soft, flexible tip 26 which facilitates the smooth insertion and positioning of the catheter through a peripheral vessel such as the left subclavian artery 22. The left subclavian artery 22 provides a smooth path for insertion and virtually directs the catheter into place in the ascending aorta 24. However, the aortic occlusion catheter is not limited to insertion through the left subclavian artery. By way of example only and not limitation, the aortic occlusion catheter alternatively may be inserted in to a brachial or axillary artery.

The diameter of the aortic occlusion catheter 20 is optimally minimized, which helps to avoid injury, plaque removal, and distortion of the aorta and the left subclavian artery. The preferred diameter of the aortic occlusion catheter is from about 7 to about 18 French. The more preferred diameter of the aortic occlusion catheter is from about 9 to about 15 French. The most preferred diameter is about 14 French.

Preferably, the aortic occlusion catheter 20 includes an inflatable balloon 28 distal to the tip 26 of the catheter. The inflatable balloon 28 is preferably elastomeric, comprising silicone or latex. Upon proper insertion of the catheter, the inflatable balloon is positioned at the base of the ascending aorta 24 just cephalid to the junction of the coronary arteries. Upon sufficient inflation, the inflatable balloon 24 occludes the ascending aorta.

In addition, the flexible tip 26 is provided with infusion outlets 34 for providing antegrade cardioplegia, as will be described in more detail herein below.

In a preferred embodiment of the present invention, the aortic occlusion catheter comprises two lumens: an inflation lumen, and a venting and infusion lumen. The inflation lumen permits the selective inflation and deflation of the inflatable balloon. Drainage and decompression for the left heart are provided by the venting and infusion lumen, which is also utilized to initially arrest the heart.

Arresting the heart is accomplished using a high concentration of potassium solution or a cardioplegia solution, either of which is infused through the aortic occlusion catheter and into the heart via the coronary arteries in the normal, or antegrade, direction of blood flow. Infusion outlets 34 allow fluid flow through the catheter for both venting and infusion.

Different surgical preferences will dictate the utilization of the combined infusion and venting lumen. For example, the lumen may initially be used as an infusion lumen to provide cardiac arrest. After the initial cardiac arrest, cardioplegia may be maintained through another catheter, while the aortic occlusion catheter provides venting of the left heart. Additionally, the cardioplegia delivery may be alternated from another catheter to the aortic occlusion catheter in intervals. In such a combination, the internal space in the lumen of the aortic occlusion catheter must preferably be cleared prior to switching from venting to infusion.

It should be understood, however, that in an alternate embodiment of the present invention, the infusion and venting lumen are separated into individual lumens.

For proper placement, the aortic occlusion catheter is inserted until the flexible tip abuts the aortic semilunar valve, and then the catheter is pulled back slightly. Upon correct positioning, the flexible tip 26 of the catheter 20 is preferably situated just proximal to the coronary arteries 30 in the left ventricle of the heart. Alternatively, placement can be fluoroscopically verified as per the preference of the surgeon.

The femoral access arterial return catheter 80 terminates in a soft flexible tip 82. The tip 82 is tapered and elongated with a plurality of exit holes 84. The exit holes 84 are sized to allow the oxygenated blood to enter the arterial system at a level conducive to perfusion of the body without the tissue damage conventionally associated with jet-like pressure. Further, the reduced diameter and decreased rate of blood flow from the femoral arterial return catheter decrease the likelihood of dislodging plaque from the arterial wall. The femoral access arterial return catheter is specifically designed to prevent such damage.

It should be appreciated that the femoral access arterial return catheter alternatively may include only one exit hole sized to allow the oxygenated blood to enter the arterial system. The rate of blood flow from the single exit hole is also designed to decrease the jet-like pressure associated with conventional arterial return cannulas.

FIG. 1 additionally illustrates the femoral access venous return catheter 60. The femoral access venous return catheter 60 terminates in an elongated and tapered tip 68 which is preferably made of a soft flexible material to reduce damage to the surrounding tissues upon insertion. The elongated tip 68 accommodates multiple inlet openings 66. These inlet openings 66 allow venous blood to drain from the right atrium 64 into the femoral access venous return catheter wherein the blood is then directed to a cardiopulmonary bypass machine for oxygenation, temperature regulation, and the like.

The femoral access venous return catheter is inserted into a femoral vein 62 and extended into the right atrium 64. The diameter of this catheter is large enough to accommodate optimum fluid flow from the right atrium and prevent back-flow into the surgical site, but still sized to facilitate ease of insertion into a femoral vein and extension into the right atrium.

Further, each catheter preferably includes a dilator to facilitate insertion into a vessel. In addition, each catheter may preferably contain barium stripes for visualization to verify placement.

To use the catheter system of the present invention, the first step preferably includes insertion and proper placement of each catheter, with any inflatable balloon in a deflated state and any valve or stop-cock in a closed position.

Once each catheter is properly positioned, the next step involves initiating cardiopulmonary bypass and stopping the heart. This may be accomplished by inflating the balloon of the aortic occlusion catheter so that it occludes the ascending aorta just cephalid to the opening of coronary arteries. Either cardioplegia or potassium solution may then be infused to stop the beating of the heart. Preferably the cardiopulmonary bypass is commenced just prior to or simultaneously with cardiac arrest. After the heart has been stopped, the aortic occlusion catheter may be utilized to vent the left ventricle.

Figure 2:
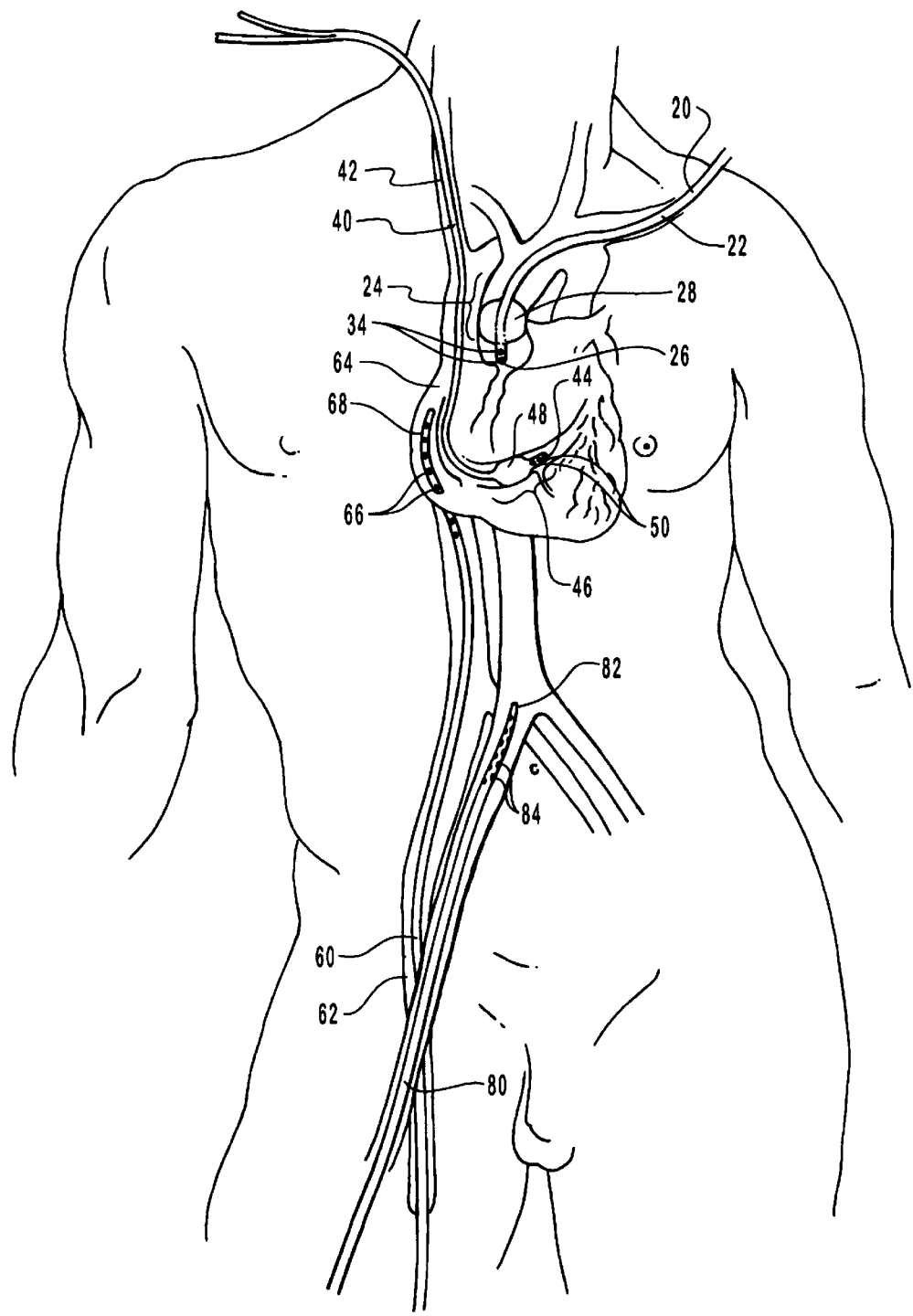
FIG. 2 is an illustration of a four-catheter system in accordance with the present invention in situ.

Alternatively, the use of four separate catheters also provides a simplified system with ease of insertion that performs total cardiopulmonary bypass with improved whole body perfusion. As illustrated in FIG. 2, wherein like features are represented by like numerals, another preferred system in accordance with the present invention comprises four specialized catheters: an aortic occlusion access catheter 20, a jugular access perfusion catheter 40, a femoral access venous return catheter 60, and a femoral access arterial return catheter 80.

Upon cardiac arrest the aortic occlusion catheter may serve as a vent to decompress the left ventricle, or may alternate with the jugular access catheter 40 to administer cardioplegia solution in intervals.

Following the initial perfusion of cardioplegia or potassium solution into the coronary arteries, the jugular access perfusion catheter 40 perfuses cardioplegia solution into the heart in the opposite, or retrograde, direction of normal fluid flow. This jugular access catheter 40 is elongated and elastomeric to facilitate insertion into a jugular vein 42 and positioning into the coronary sinus 46.

The jugular access perfusion catheter 40 terminates in a soft, flexible tip 44 which also aids in insertion and positioning. Upon proper insertion, the tip 44 of the jugular access perfusion catheter is situated in the coronary sinus 46.

A perfusion lumen runs the length of the jugular access perfusion catheter to direct the flow of cardioplegia out through apertures 38 in the tip 44 and into the coronary sinus.

The jugular access perfusion catheter 40 employs a balloon 48 just proximal to the tip 44. This balloon 48 is preferably positioned immediately within the coronary sinus 46 which occludes fluid flow from the coronary sinus into the right atrium and helps to retain the catheter in place. Along these lines, the balloon 48 may include knobs or protuberances which serve as retention means to further ensure proper retention in the coronary sinus. U.S. Pat. No. 5,423,745 by Todd teaches such retention means and is herein incorporated by reference in its entirety.

Additionally, an inflation lumen is provided in the jugular access perfusion catheter 40 for inflation of the balloon 48.

Figure 3:
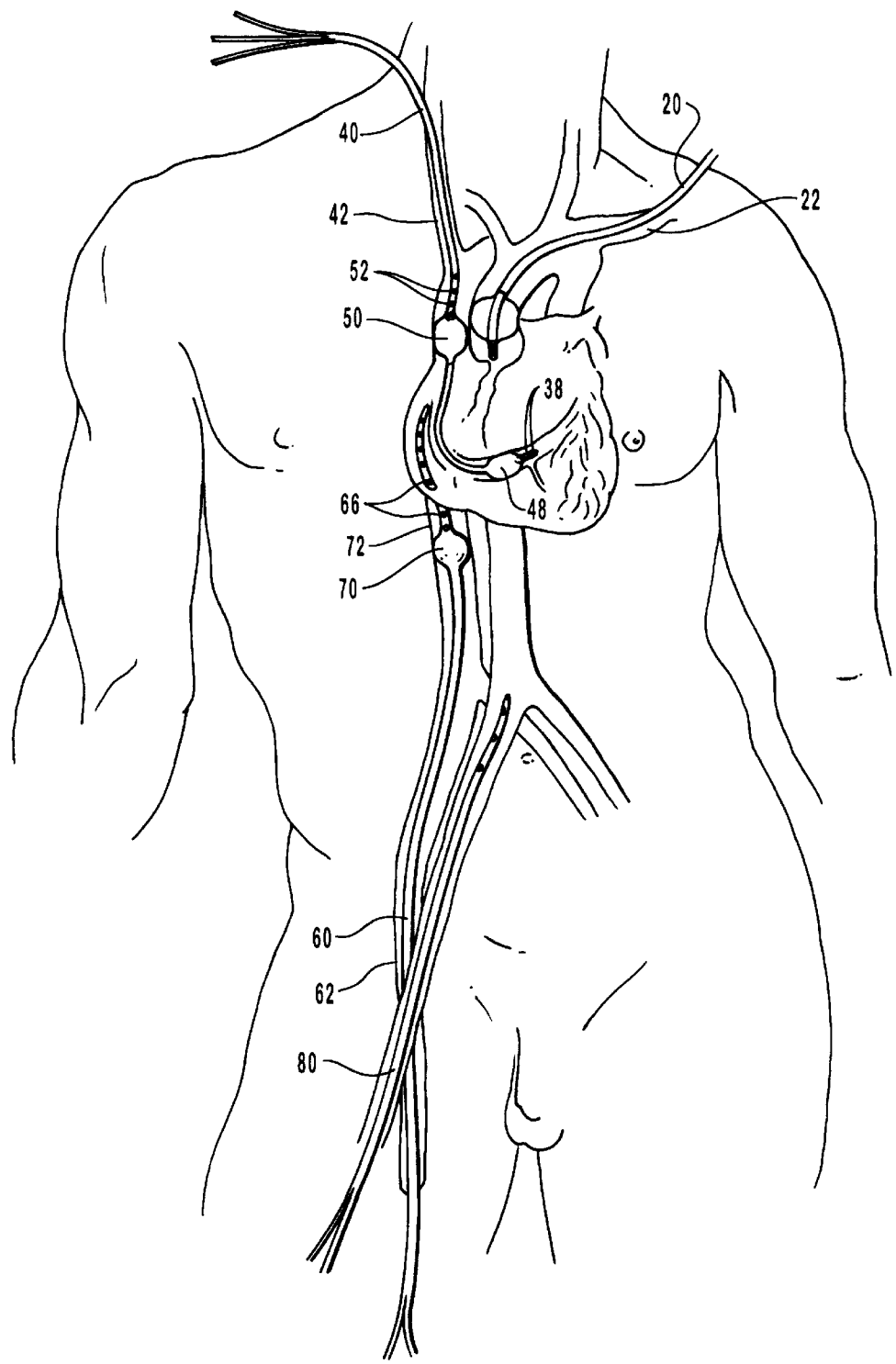
FIG. 3 is an illustration of another embodiment of a four-catheter system in accordance with the present invention in situ.

FIG. 3 illustrates an alternate embodiment of the present invention wherein the jugular access perfusion catheter employs a second inflation balloon 50 positioned to occlude the superior vena cava. This balloon 50 is preferably positioned just cephalid to the opening of the superior vena cava into the right atrium. Balloon 50 further employs a separate inflation lumen. In addition, balloon 50 necessitates a vent and a venting lumen in the jugular access perfusion catheter just cephalid to the second balloon. Multiple inlets 52 are included for the venous blood return.

Such positioning of the balloon helps to isolate the right atrium during cardiac surgical procedures. For instance, isolation of the right atrium provides optimal conditions for valve replacement procedures.

Additionally, FIG. 3 illustrates the femoral access venous return catheter 60 equipped with an inflatable balloon 70. This balloon is preferably positioned in the inferior vena cava 72 just caudal to the entrance of the inferior vena cava into the right atrium. Both an inflation lumen and a venting lumen are also incorporated into the catheter in this embodiment.

Such placement of a balloon 70 facilitates isolation of the right atrium. Because of the important cardiac surgical procedures that benefit from right atrial isolation, it should also be appreciated that such a balloon could be located on a different or separate peripherally inserted catheter.

To use the catheter system of the present embodiment, the first step preferably includes insertion and proper placement of each catheter, with any inflatable balloon in a deflated state and any valve or stop-cock in a closed position.

Once each catheter is properly positioned, the next step involves initiating cardiopulmonary bypass and stopping the heart. This may be accomplished by inflating the balloon of the aortic occlusion catheter so that it occludes the ascending aorta just cephalid to the opening of coronary arteries. Either cardioplegia or potassium solution may then be infused to stop the beating of the heart. The balloon of the jugular access perfusion catheter should be inflated to occlude the coronary sinus. Preferably the cardiopulmonary bypass is commenced just prior to or simultaneously with cardiac arrest. After the heart has been stopped, the aortic occlusion catheter is utilized to vent the left ventricle and the jugular access profusion catheter perfuses cardioplegia solution into the coronary sinus.

Alternatively, the aortic occlusion catheter and the jugular access perfusion catheter may provide cardioplegia solution to the heart in intervals.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A system for employing blood management during cardiac surgical procedures comprising at least:
   a. an aortic occlusion catheter designed for percutaneous introduction into a peripheral vessel and for antegrade introduction of cardioplegia solution into the coronary arteries, said aortic occlusion catheter being advantageously positioned in the ascending aorta, and further providing a balloon positioned at the base of the ascending aorta just cephalid to the junction of the coronary arteries, said balloon providing for occlusion of the ascending aorta upon inflation;
   b. a femoral access arterial return catheter designed for percutaneous introduction into a femoral artery, said femoral access arterial return catheter positioned within a femoral artery and extended slightly therein to facilitate perfusion of the body with oxygenated blood, and terminating in a flexible tip comprising at least one exit hole designed to deter expulsive oxygenated blood flow therefrom; and
   c. a femoral access venous return catheter designed for percutaneous introduction into a femoral vein, said femoral access venous return catheter terminating in a flexible tip comprising a plurality of inlet openings to accommodate venous blood drainage from a right atrium.

2. A system as recited in claim 1, wherein said femoral access venous return catheter is equipped with an inflatable balloon positioned caudal to the entrance of the inferior vena cava in the right atrium such that isolation of the right atrium is facilitated.

3. A system as recited in claim 1, further comprising a jugular access perfusion catheter positioned for directing flow of cardioplegia into the coronary sinus.

4. A system as recited in claim 3, wherein said jugular access perfusion catheter comprises a balloon positioned within the coronary sinus such that fluid flow is occluded from the coronary sinus into the right atrium.

5. A system as recited in claim 4, wherein said jugular access perfusion catheter comprises an inflation balloon positioned cephalid to the opening of the superior vena cava into the right atrium such that isolation of the right atrium is facilitated.

6. A system as recited in claim 1, wherein said aortic occlusion catheter terminates in a flexible tip positioned just proximal to a patient's coronary arteries.

7. A system as recited in claim 1, wherein said aortic occlusion catheter further comprises a diameter which is minimized for avoiding injury, plaque removal, and distortion of the aorta and the axillary, brachial and left subclavian arteries.

8. A system as recited in claim 7, wherein said diameter is from about 7 to about 18 French.

9. A system as recited in claim 7, wherein said diameter is from about 9 to about 15 French.

10. A system as recited in claim 7, wherein said diameter is about 14 French.

11. A system as recited in claim 1, wherein said aortic occlusion catheter comprises three lumens.

12. A system as recited in claim 1, wherein said aortic occlusion catheter comprises two lumens.

13. A system as recited in claim 1, wherein said aortic occlusion catheter is designed to provide venting of the left heart.

14. A method for employing blood management during cardiac surgical procedures comprising the steps of:
  a. inserting an aortic occlusion catheter comprising a flexible tip, an inflatable balloon positioned at the base of the ascending aorta just cephalid to the junction of the coronary arteries, and at least one infusion outlet positioned proximal to said balloon, into a peripheral vessel;
    i. advancing the aortic occlusion catheter until the tip abuts the aortic semilunar valve,
    ii. pulling back on the aortic occlusion catheter such that the tip is just proximal to the coronary arteries and said inflatable balloon is positioned in the ascending aorta,
    iii. inflating said inflatable balloon to occlude the ascending aorta,
    iv. arresting the heart utilizing antegrade infusion of cardioplegia solution, and
    v. venting the left heart;
  b. inserting a femoral access arterial return catheter comprising a flexible tip including at least one exit hole designed to deter expulsive oxygenated blood flow therefrom into a femoral artery;
  c. inserting a femoral access venous return catheter comprising a flexible tip including a plurality of inlet openings for accommodating venous blood drainage from the right atrium into a femoral vein; and
  d. initiating cardiopulmonary bypass.

15. A method as recited in claim 14, wherein said femoral access venous return catheter is equipped with an inflatable balloon positioned caudal to the entrance of the inferior vena cava in the right atrium.

16. A method as recited in claim 15, further comprising the step of inflating the inflatable balloon of the femoral access venous return catheter to isolate the right atrium.

17. A method as recited in claim 14, further comprising a jugular access perfusion catheter positioned for directing flow of cardioplegia solution into the coronary sinus, and comprising a balloon positioned within the coronary sinus.

18. A method as recited in claim 17, further comprising the step of inflating the balloon positioned within the coronary sinus to occlude fluid flow from the coronary sinus into the right atrium.

19. A method as recited in claim 18, further comprising the step of perfusing the heart with cardioplegia solution through said jugular access perfusion catheter.

20. A method as recited in claim 17, wherein said jugular access perfusion catheter comprises an inflation balloon positioned cephalid to the opening of the superior vena cava into the right atrium.

21. A method as recited in claim 20, further comprising the step of inflating the inflation balloon of said jugular access perfusion catheter for isolation of the right atrium.

22. A method as recited in claim 14, wherein said peripheral vessel is the left subclavian artery.

23. A method as recited in claim 14, wherein said peripheral vessel is an axillary artery.

24. A method as recited in claim 14, wherein said peripheral vessel is a brachial artery.

25. A method as recited in claim 14, wherein said aortic occlusion catheter further comprises a diameter which is minimized for avoiding injury, plaque removal, and distortion of the aorta and the left sublavian, axillary, and brachial arteries.

26. A system for employing blood management during cardiac surgical procedures comprising:
  a. an aortic occlusion catheter designed for percutaneous introduction into a peripheral vessel and for antegrade introduction of cardioplegia solution into the coronary arteries, said aortic occlusion catheter being advantageously positioned in the ascending aorta and further providing a balloon positioned at the base of the ascending aorta just cephalid to the junction of the coronary arteries, said balloon providing for occlusion of the ascending aorta upon inflation;
  b. a femoral access arterial return catheter designed for percutaneous introduction into a femoral artery, said femoral access arterial return catheter positioned within a femoral artery and extended slightly therein to facilitate perfusion of the body with oxygenated blood, and said femoral access arterial perfusion catheter terminating in a flexible tip comprising at least one exit hole designed to deter expulsive oxygenated blood flow therefrom;
  c. a femoral access venous return catheter designed for percutaneous introduction into a femoral vein, said femoral access venous return catheter terminating in a flexible tip comprising a plurality of inlet openings to accommodate venous blood drainage from a right atrium; and
  d. a jugular access perfusion catheter positioned for directing flow of cardioplegia solution into the coronary sinus, said jugular access perfusion catheter further including a balloon positioned within the coronary sinus such that fluid flow is occluded from the coronary sinus into the right atrium.

27. A system as recited in claim 26, wherein said femoral access venous return catheter is designed for extension into a right atrium.

28. A system as recited in claim 26, wherein said femoral access venous return catheter is equipped with an inflatable balloon positioned caudal to the entrance of the inferior vena cava in the right atrium such that isolation of the right atrium is facilitated.

29. A system as recited in claim 26, wherein said jugular access perfusion catheter comprises an inflation balloon positioned cephalid to the opening of the superior vena cava into the right atrium such that isolation of the right atrium is facilitated.

30. A method for employing blood management during cardiac surgical procedures comprising the steps of:
   a. inserting an aortic occlusion catheter comprising a flexible tip, an inflatable balloon positioned at the base of the ascending aorta just cephalid to the junction of the coronary arteries, and at least one infusion outlet positioned proximal to said balloon, into a peripheral vessel;
      i. advancing the aortic occlusion catheter until the tip abuts the aortic semilunar valve,
      ii. pulling back on the aortic occlusion catheter such that the tip is just proximal to the coronary arteries and said inflatable balloon is positioned in the ascending aorta,
      iii. inflating said inflatable balloon to occlude the ascending aorta,
      iv. arresting the heart utilizing antegrade infusion of cardioplegia solution, and
      v. venting the left heart;
   b. inserting a femoral access arterial return catheter comprising a flexible tip including at least one exit hole designed to deter expulsive oxygenated blood flow therefrom into a femoral artery;
   c. inserting a femoral access venous return catheter comprising a flexible tip including a plurality of inlet openings for accommodating venous blood drainage from the right atrium into a femoral vein;
   d. inserting a jugular access perfusion catheter comprising a balloon positioned within the coronary sinus into a jugular vein, and
      i. inflating the balloon of the jugular access catheter to occlude fluid flow from the coronary sinus into the right atrium; and
   e. initiating cardiopulmonary bypass.

31. A method as recited in claim 30, wherein said femoral access venous return catheter is equipped with an inflatable balloon positioned caudal to the entrance of the inferior vena cava in the right atrium.

32. A method as recited in claim 31, further comprising the step of inflating the inflatable balloon of the femoral access venous return catheter to isolate the right atrium.

33. A method as recited in claim 30, wherein said jugular access perfusion catheter comprises an inflation balloon positioned cephalid to the opening of the superior vena cava into the right atrium.

34. A method as recited in claim 33, further comprising the step of inflating the inflation balloon of said jugular access perfusion catheter for isolation of the right atrium.

35. A method as recited in claim 33, further comprising the step of perfusing the heart with cardioplegia solution through said jugular access perfusion catheter.

36. A method as recited in claim 30, wherein said peripheral vessel is the left subclavian artery.

37. A method as recited in claim 30, wherein said peripheral vessel is an axillary artery.

38. A method as recited in claim 30, wherein said peripheral vessel is a brachial artery.

39. A method as recited in claim 30, wherein said aortic occlusion catheter further comprises a diameter which is minimized for avoiding injury, plaque removal, and distortion of the aorta and the left subclavian, brachial and axillary arteries.

40. A system as recited in claim 1, wherein the peripheral vessel into which the aortic occlusion catheter is designed to be introduced is the left subclavian artery.

\* \* \* \* \*